United States Patent
Fortin et al.

(10) Patent No.: US 7,267,692 B2
(45) Date of Patent: Sep. 11, 2007

(54) NUCLEUS PROSTHESIS, THE INSERTION DEVICE THEREFOR AND THE METHOD OF FITTING SAME

(76) Inventors: Frederic Fortin, 36, allée des Passerines, F-33600 Pessac (FR); Johann Robin, 1, allée du Puits de Maran, F-33130, Bègles (FR)

( * ) Notice: Subject to any disclaimer, the term of this patent is extended or adjusted under 35 U.S.C. 154(b) by 0 days.

(21) Appl. No.: 10/800,083

(22) Filed: Mar. 11, 2004

(65) Prior Publication Data
US 2005/0015151 A1    Jan. 20, 2005

Related U.S. Application Data

(63) Continuation of application No. PCT/FR02/03103, filed on Sep. 12, 2002.

(30) Foreign Application Priority Data
Sep. 14, 2001    (FR) .................................. 01 11905

(51) Int. Cl.
*A61F 2/44* (2006.01)
(52) U.S. Cl. .................................. 623/17.16
(58) Field of Classification Search ........ 623/17.11–16
See application file for complete search history.

(56) References Cited

U.S. PATENT DOCUMENTS

| | | | | |
|---|---|---|---|---|
| 3,875,595 A | * | 4/1975 | Froning .................... | 623/17.12 |
| 4,413,359 A | * | 11/1983 | Akiyama et al. ......... | 623/23.72 |
| 4,433,440 A | * | 2/1984 | Cohen ......................... | 623/8 |
| 4,529,332 A | * | 7/1985 | Glabiszewski ............. | 403/366 |
| 4,636,213 A | * | 1/1987 | Pakiam ..................... | 623/8 |
| 4,648,880 A | * | 3/1987 | Brauman ................. | 623/8 |
| 4,969,888 A | * | 11/1990 | Scholten et al. ........... | 606/94 |
| 5,047,055 A | | 9/1991 | Bao et al. | |
| 5,571,189 A | * | 11/1996 | Kuslich ................... | 623/17.12 |
| 5,601,556 A | * | 2/1997 | Pisharodi ................ | 606/61 |
| 5,645,597 A | | 7/1997 | Krapiva | |
| 5,697,977 A | * | 12/1997 | Pisharodi ................ | 606/61 |
| 5,800,549 A | | 9/1998 | Bao et al. | |
| 5,888,228 A | * | 3/1999 | Knothe et al. ............. | 623/17.16 |
| 5,972,015 A | | 10/1999 | Scribner et al. | |
| 6,066,154 A | * | 5/2000 | Reiley et al. .............. | 606/192 |
| 6,102,950 A | * | 8/2000 | Vaccaro ................... | 623/17.16 |
| 6,168,631 B1 | * | 1/2001 | Maxwell et al. .......... | 623/21.18 |
| 6,402,784 B1 | * | 6/2002 | Wardlaw ................. | 623/17.11 |
| 6,419,704 B1 | * | 7/2002 | Ferree ..................... | 623/17.12 |
| 6,436,142 B1 | * | 8/2002 | Paes et al. ............... | 623/17.15 |

(Continued)

FOREIGN PATENT DOCUMENTS

EP    0 100 127 A1    2/1984

(Continued)

*Primary Examiner*—Eduardo C. Robert
*Assistant Examiner*—Annette R. Reimers (57) ABSTRACT

A device (3) used to fit a nucleus prosthesis made up of: a deformable elastic nucleus prosthesis (1) which can adapt to the shape of intervertebral cavities, the prosthesis consisting of two parts, namely a male part (11) and a female part (12); and an insertion assembly (2) which is connected to the nucleus prosthesis (1). The elastic deformation of the nucleus prosthesis (1) makes it possible for the prosthesis to be inserted into the intervertebral cavity. The prosthesis is inserted using the elasticity thereof and the insertion means (2) which form part of the device (3) before insertion, but which can be subsequently removed.

10 Claims, 8 Drawing Sheets

U.S. PATENT DOCUMENTS

| | | |
|---|---|---|
| 6,620,196 B1 | 9/2003 | Trieu |
| 6,733,533 B1 * | 5/2004 | Lozier .................... 623/17.12 |
| 2002/0099444 A1 * | 7/2002 | Boyd et al. ............. 623/17.16 |
| 2002/0120334 A1 * | 8/2002 | Crozet .................... 623/17.11 |
| 2002/0147497 A1 * | 10/2002 | Belef et al. ............. 623/17.12 |
| 2003/0004574 A1 * | 1/2003 | Ferree .................... 623/17.12 |
| 2003/0004576 A1 * | 1/2003 | Thalgott ................. 623/17.16 |
| 2003/0028197 A1 * | 2/2003 | Hanson et al. ............. 606/99 |
| 2003/0060825 A1 * | 3/2003 | Alfaro et al. ................ 606/61 |
| 2004/0127992 A1 | 7/2004 | Hassan |

FOREIGN PATENT DOCUMENTS

| | | |
|---|---|---|
| EP | 0 621 020 A1 | 10/1994 |
| EP | 0 919 209 A1 | 6/1999 |
| EP | 1 132 031 A2 | 9/2001 |

* cited by examiner

NUCLEUS PROSTHESIS, THE INSERTION DEVICE THEREFOR AND THE METHOD OF FITTING SAME

CROSS REFERENCE TO RELATED APPLICATIONS:

This application is a continuation of U.S. application Ser. No., PCT/FR02/03103, filed on Sep. 12, 2002, of the same title, and claims priority under the Paris Convention to French patent application 01/11905, filed on Sep. 14, 2001, the contents of which are herein incorporated by reference thereto.

FIELD OF THE INVENTION

The present invention concerns an intervertebral disk prosthesis and means for its insertion as well as an insertion procedure. This prosthesis, after insertion and removal of the means of insertion, replaces the nucleus of the existing cavity after partial or total ablation of the latter by preserving the ring of the intervertebral disk concerned.

PRIOR ART

We would like to briefly bring to mind the construction of an intervertebral disk linking to vertebral bodies and whose functioning is complex. This disk is comprised of a centrally located nucleus pulposus and of an annulus fibrosus—peripherical structure containing the nucleus and solidly bringing together the vertebral plates. As all the elastic links of the human body, the intervertebral disks are subject to degeneration, particularly those of the lumbar vertebral column which are most often subjected to stress.

Most of the pathologies of the disk come from the fissure of the annulus which lets part of the nucleus escape, the latter then forms a flange which is often in contact with the nervous system, where the most sensitive area of the annulus is. This disk hernia will press the nervous roots or the dura mater and causes intense pains and can even lead to paralysis.

However, a degenerated disk can be treated by replacing the whole or part of the nucleus and the damaged annulus. Many invasive systems replace the totality of the nucleus as well as the major part of the annulus. However, even if these reproduce the adequate mechanic responses, they all have the inconvenience of being very difficult to anchor, forcing the operator to add external elements to the prosthesis which are fixed to the vertebras. These metallic pieces cause the organism to react, which will tend to block movements and the prosthesis becomes inoperable.

Patent EP 0,919,209 describes a nucleus prosthesis comprised of dry hydrogel, which after implantation will take on water and swell by at least one millimetre in height. The incision of the annulus must be in this case larger in order to let the block pass, thus diminishing its function as a barrier wall, the inventors then proposed to place two smaller blocks, each block entering one another by a small opening, in this case the blocks don't have any mechanic link and there remain empty spaces inside the cavity which cannot be filled in any way. With so many constraints appearing on the already damaged annulus, this places in doubt the lifespan of the implant and the viability of the annulus.

Patent application No. 0,100,127 solves the problem by means of an elastic envelope, by an opening in the annulus which will adjust to the cavity by elastic expansion. A viscose filling material must be then injected which by being polymerised will fill the prosthesis and thus fill the cavity. This operation requires a supplementary injection step which, in certain cases can be constraining in that it increases operation time.

Patent EP0621 020 A is essentially based on the insertion means which in this case are specifically adapted to ball-type spherical materials and which do not resemble the elastic, form-adjustable materials which are the core of the present invention, the former not at all making unpatentable the latter.

The U.S. Pat. No. 5,800,549A is a force generator for the injection of a vertebral-column implant, the means put into operation are different from those of the present invention which uses extremely simple means based on readily available materials.

U.S. Pat. No. 5,645,597 A describes a method enabling the withdrawal of the nucleus, then a prosthesis comprised of an elastic ring covered by two membranes, the ring having a hole for the passage of a gel introduced with a syringe which will fill the centre of the prosthetic cavity. In the present invention, the prosthesis is comprised of two parts out of which each part is perfectly polymerised before being separately introduced and precisely guided in relation to one another.

Patent EP 1132031 A solves a different problem from that solved in the present patent application, in that in this prior art the question is to make a graft grow on a damaged bone, the injected particles are of the non-malleable bone, which has nothing to do with the problem that the present application wishes to resolve.

SUMMARY OF THE INVENTION

The invention relates to a device that is used to fit a nucleus prosthesis comprising: a deformable elastic nucleus prosthesis which can adapt to the shape of intervertebral cavities, said prosthesis consisting of two parts, namely a male part and a female part; and an insertion assembly which is connected to the nucleus prosthesis. The elastic deformation of the inventive nucleus prosthesis makes it possible for the prosthesis to be inserted into the intervertebral cavity. According to the invention, said prosthesis is inserted using the elasticity thereof and the insertion means which form part of the device before insertion but which can be subsequently removed. The invention also relates to different forms of prosthesis and insertion devices.

The present invention does not require any product injection, it solves the posed problem by means which are completely different from this prior art, the latter not taking away from the novelty and the inventive activity of the present invention in any way.

None of the documents examined so far have attempted to connect the characteristics of the nucleus prosthesis to the means of insertion used.

BRIEF DESCRIPTION OF THE DRAWINGS

The drawings, serving to understand the invention, are.

DETAILED DESCRIPTION OF THE PREFERRED EMBODIMENT(S)

Figure 1:
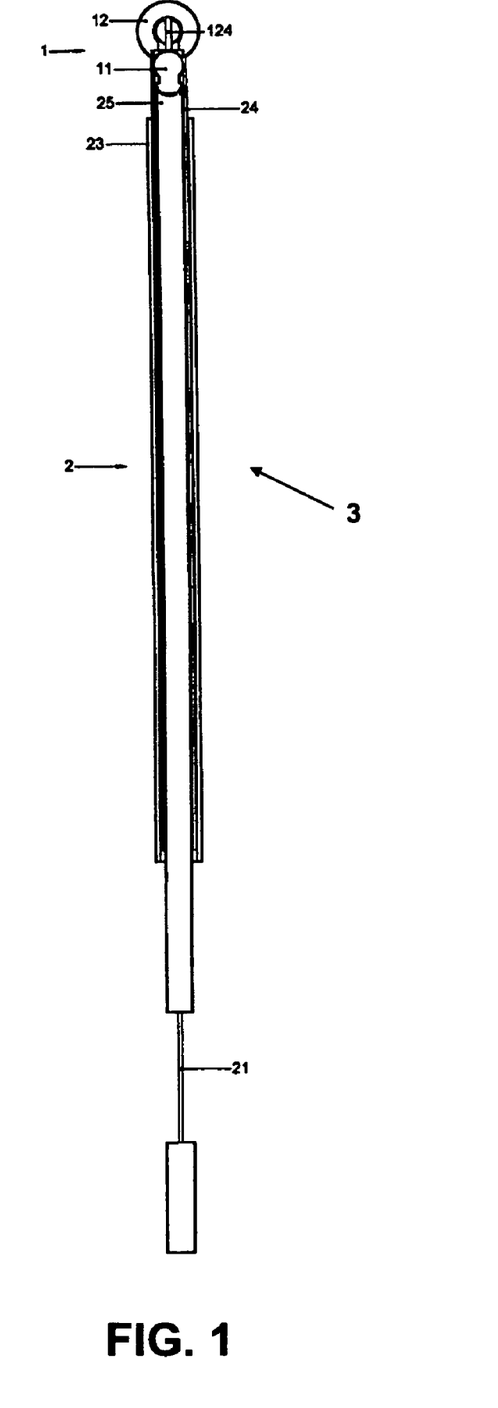
FIG. 1 of sheet 1/8 is a cross-section of the complete device (prosthesis and means of insertion).
Figure 2:
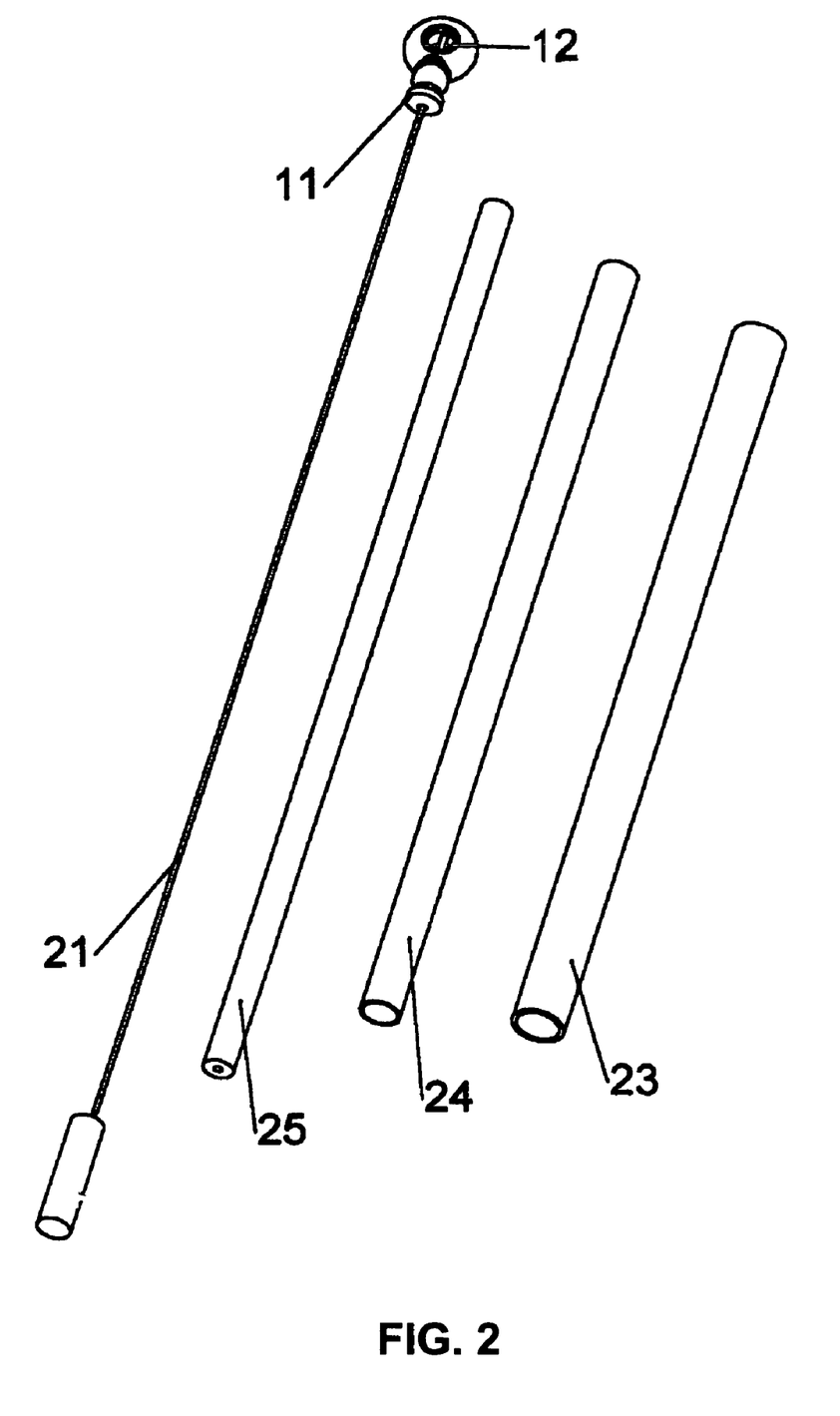
FIG. 2 of sheet 2/8 is an exploded view of the means which make up the invention.

Device 3 for the installation of a nucleus prosthesis together with its insertion means includes, in a first embodiment, nucleus prosthesis 1 an insertion assembly 2

Figure 3:
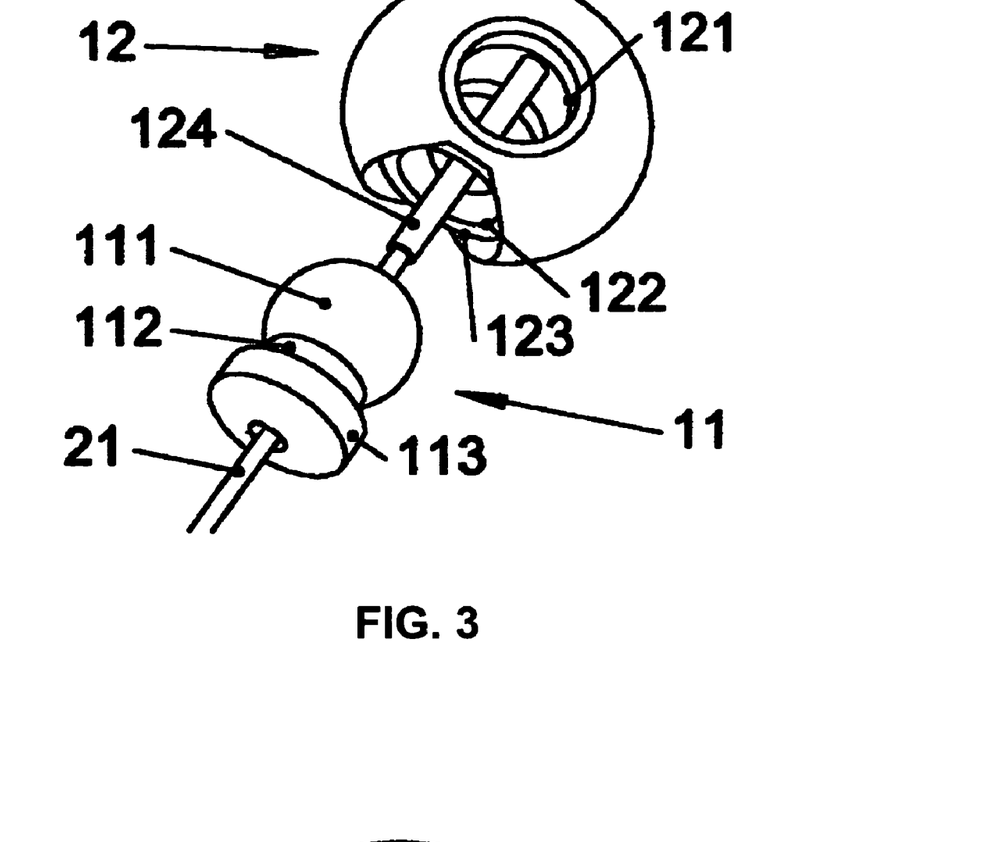
FIG. 3 of sheet 3/8 is a perspective view of the prosthesis comprised of two distinct parts.
Figure 4:
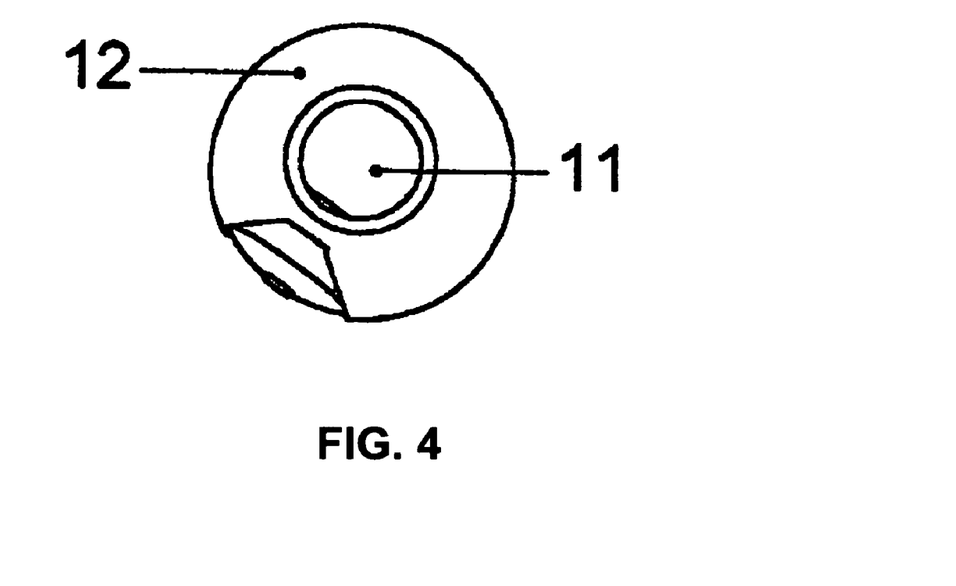
FIG. 4 of sheet 3/8 is a perspective view of the prosthesis after the joining of the two parts.
Figure 5A:
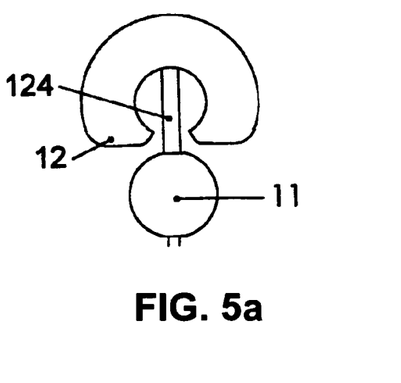
FIG. 5a of sheet 4/8 is a horizontal cross-section of the prosthesis comprised of 2 parties before assembly.
Figure 5B:
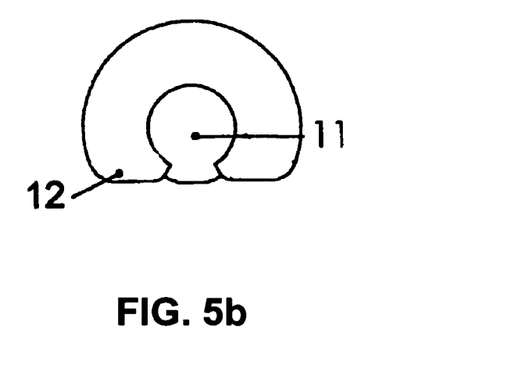
FIG. 5b of sheet 4/8 is a horizontal cross-section of the prosthesis comprised of 2 joint parties.
Figure 6A:
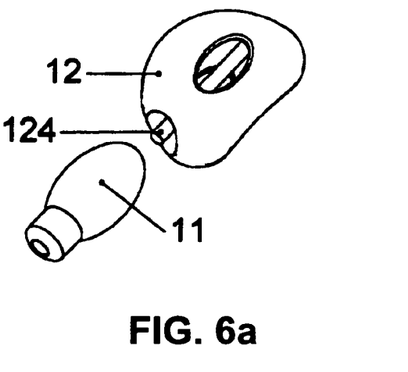
FIG. 6a of sheet 4/8 is a perspective view of a prosthesis of a different form from the original one.
Figure 6B:
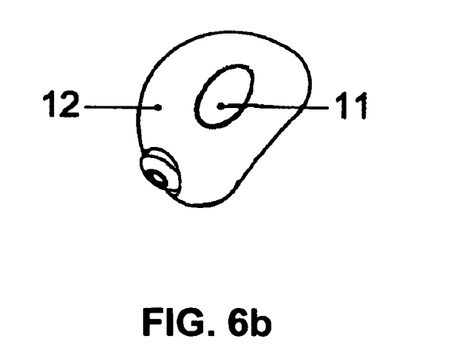
FIG. 6b of sheet 4/8 is the same prosthesis assembled, the male part having been introduced into the female part.

Means 1 is itself formed of means 12 referred to as the female part, made out of elastically deformable material whose form may be a hollow sphere with flattened poles, formed:

of a central cavity 121 connected to a rigid stem 21, of an introduction opening 122, of a means 11 male part which comprises a full, deformable sphere 111 whose main functions are:

to draw aside the female part 12 in order to introduce itself and perfectly fit the shape of cavity 121 after its introduction, to be ready to support the imposed mechanical strains.

This means 11 has in its rearward part a flange 113 whose form is determined so as to be embedded in the opening 122 which elastically deforms during the introduction. Once this operation is carried out, the male part 11 takes its definitive place and cannot be expelled from the female part 12.

The nucleus prosthesis 1 is introduced into the cavity 4 between adjacent vertebrae (ie., intervertebrally) by an insertion assembly 2 allowing its introduction, namely:

the rigid stem 21 connected to means 12 through the intermediary of a flexible connection 124 some tubes 23, 24 and 25 being used to introduce means 1 into the cavity. The tube 23 contains the female part 12 of the prosthesis 1 compressed with its guidance stem 21; it also contains the tube 24.

The tube 24 contains the male part 11 guided by stem 21, this mean 24 will be used as a push rod for the female part 12 compressed inside the tube 23.

Tube 25 threaded on stem 21 is used as a push rod for the male part 11 towards the female part 12.

Figure 8:
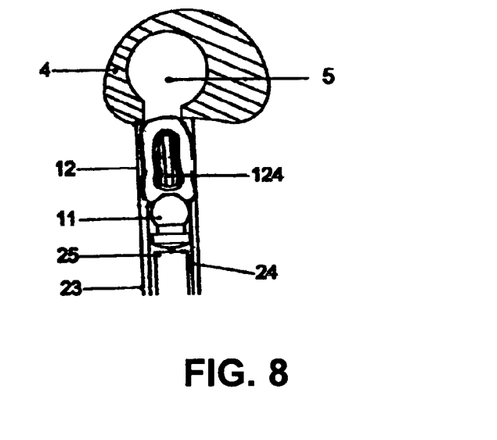
FIG. 8 of sheet 5/8 shows an assembly of components that take part in the invention before the introduction into the intervertebral disc.
Figure 9:
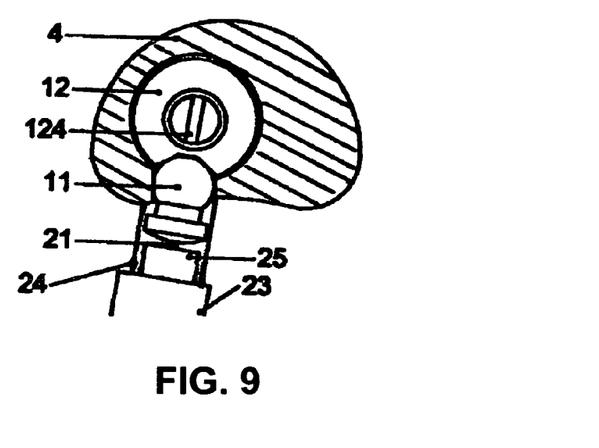
FIG. 9 of sheet 5/8 shows the assembly of means after the introduction of the female part into the intervertebral disc.
Figure 10:
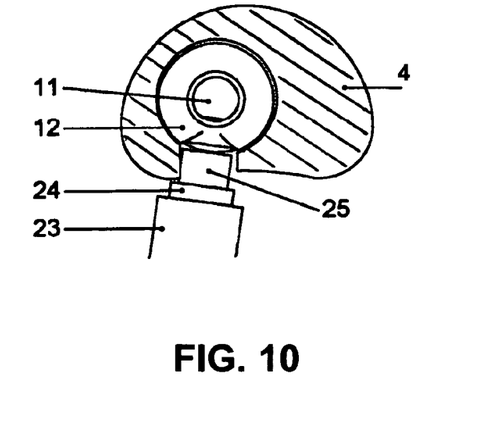
FIG. 10 of sheet 5/8 is the same prosthesis as that of FIG. 9, but after the introduction of the male part into the female part.
Figure 11:
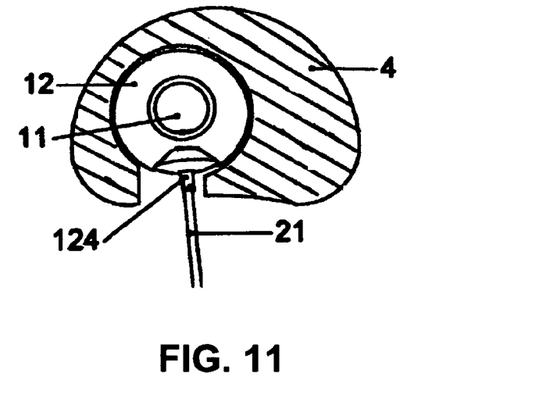
FIG. 11 of sheet 5/8 represents the same prosthesis once certain means used for insertion are withdrawn.
Figure 12:
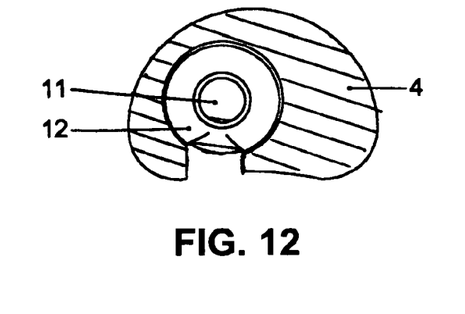
FIG. 12 of sheet 5/8 shows the prosthesis once in place, the guidance stems having been cut.
Figure 13:
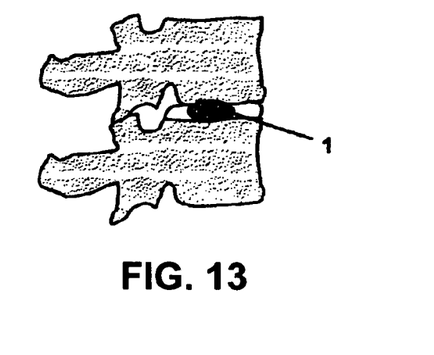
FIG. 13 of sheet 5/8 shows a longitudinal cross-section of the prosthesis placed in the intervertebral disc.
Figure 17:
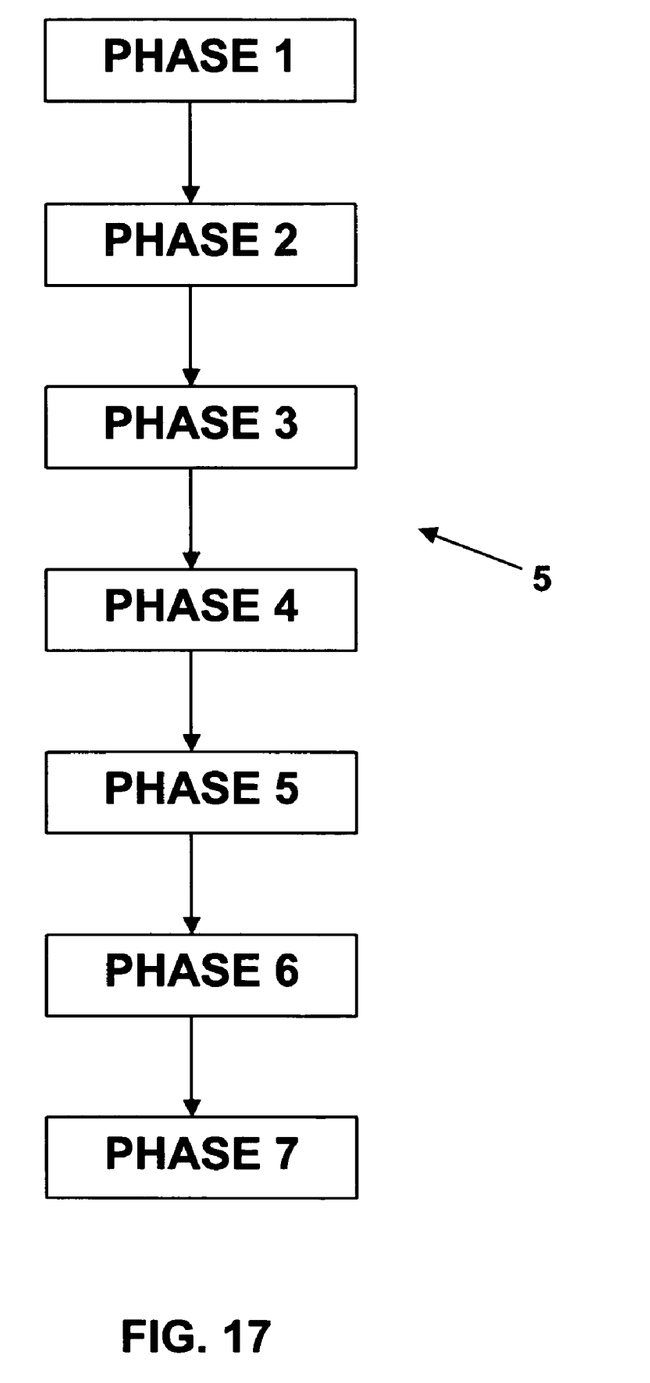
FIG. 17 of sheet 7/8 show the steps of the installation method.

The method of insertion 5 includes 7 steps;

step 1: introduction into the tube 24 of the male part 11 threaded on the stem 21;

step 2: sliding of the tube 23 around the tube 24, the female part 12 is introduced into the tube 23;

step 3: presentation of the insertion device 1 before the opening of the cavity to fill;

step 4: pushing of the female part 12 by the tube 24 (FIG. 9); step 5: introduction of tube 25 threaded on stem 21 to bring the male part 11 into the opening 122 of the female part 121;

step 6: pushing using tube 25 of the male part 11 into the opening 122 to embed means 11 in means 12;

step 7: tubes 23, 24, 25 are withdrawn, stem 21 being removed, for example by a cut at the level of the flexible connection 124, which releases prosthesis 1 of the insertion device 2. The shapes of the nucleus prostheses' 1 male parts 11 and female parts 12 can have several alternatives, always compatible with the same insertion procedure 5.

Figure 7A:
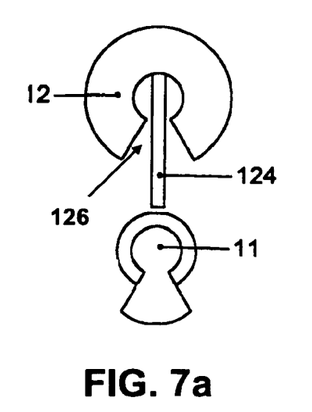
FIGS. 7a and 7b of sheet 4/8 present the same situations as FIGS. 6a and b, the female part being in this case a ring split from one part to another in sectors.
Figure 7B:
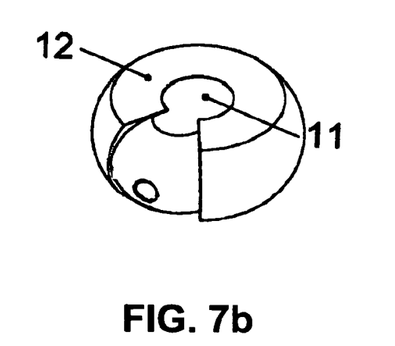

The female part 12 can have an opening 122 which can be either a circular form or the shape of a slit traversing through the prosthesis 12 in sectors, which is presented in the form of a split ring.

There always exists in this opening 122 a constriction 123, which will prohibit the male part 11 from being expelled once positioned in the female part 12. The external forms of the envelope, when not under strain, can vary, the essential function being to adapt to the cavity, intervertebrally, to fill without risk of slip or expulsion.

Figure 14:
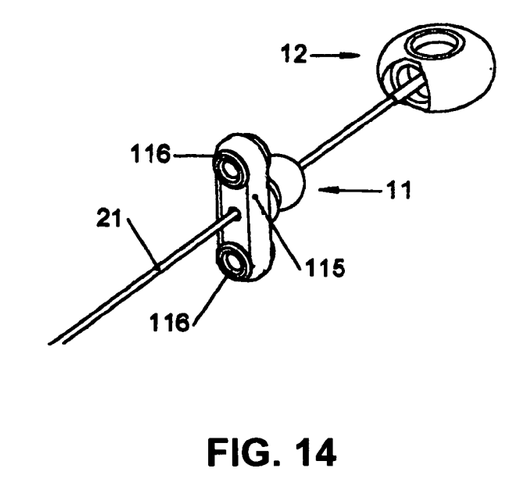
FIGS. 14, 15 and 16 of sheet 6/8 show a prosthesis in which the male part is a variant which allows for fixing on the bone.
Figure 15:
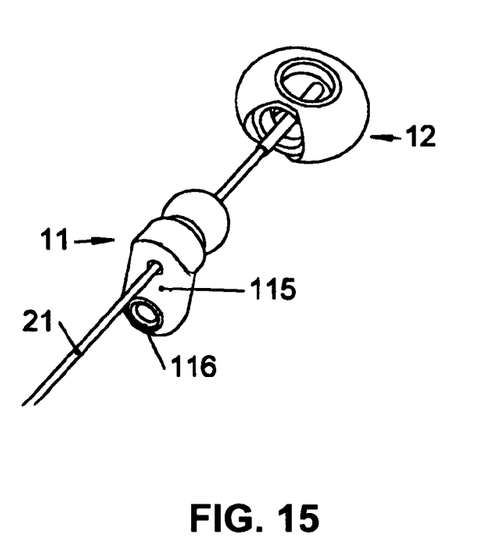
Figure 16:
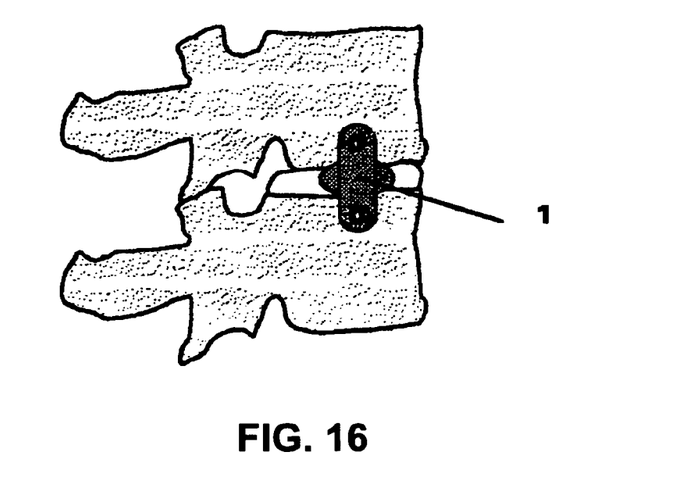

The male part 11 (FIGS. 14 and 15) can comprise at its end a flange 115 which comprises a fixing 116 on the bones, for example: holes allowing fastening screws to pass, in order to better guarantee in certain cases the non-expulsion of the prosthesis. The female part, due to its adaptation of form coming from its nature as an elastic material, may have a capacity of deformation which enables it to pass through tubes and openings of insertion which have more reduced sections, one can appreciate the ratio reduction or compression (relationship between the expanded diameter and the contracted diameter, before and after installation in the tube) is greater than 2.

Figure 18:
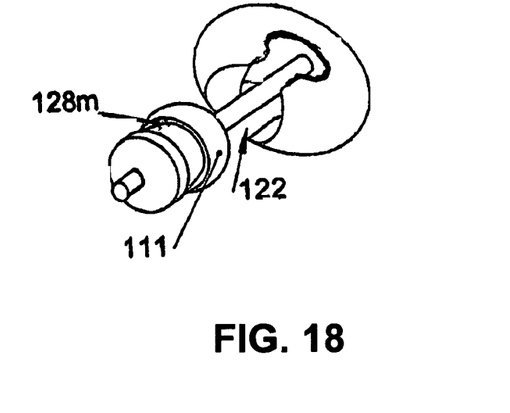
FIGS. 18 and 19 of sheet 8/8 are perspective views for the assembly of another embodiment of the prosthesis showing components before insertion.
Figure 19:
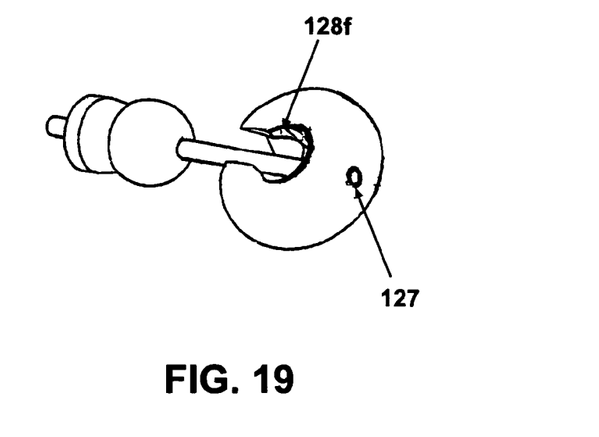

In another embodiment (see FIGS. 18, 19, 20, 21 and 22) the elastically deformable nucleus prosthesis 1 includes two parts;

a means 12, referred to as a female part, having the shape of an open ring in order to let in a male part 11, the means 12 comprises a threading 127f receiving a guidance stem 21 whose end is threaded with a threading 127 (male threading 127m corresponding to 127f), the aforementioned rigid stem 21 makes it possible to freely guide the male part 11 of the prosthesis 1 until its insertion and also to withdraw stem 21 by simple unscrewing, once prosthesis 1 is in place.

Means 12 includes an opening 122 allowing the introduction of means 11 (male part 127m). Means 11 preferably has the shape of a one way cork, it comprises a full deformable spherical head 111 as well as, if necessary, a slightly extending cylindrical body, and is placed at the periphery of the ring.

Figure 20:
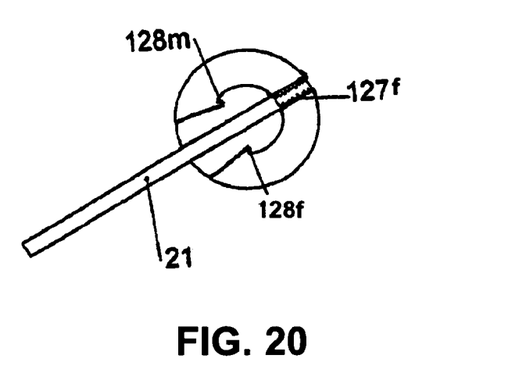
FIG. 20 of sheet 8/8 is a cross-section (in the shape of a champagne cork) of a male and female prosthesis in place.

In this solution, the anchoring of the male part 11 in the female part is ensured by a one way system of overlapping of the male parts 128m and female parts 128f, a system integrated into the shape of the parts during manufacture.

Upon the introduction, the male part 11 draws aside opening 122 of the ring, the latter, due to elasticity, afterwards comes to be closed again on the male part 11. Moreover, (see FIG. 22) the spherical head of the male part slightly exceeds the thickness of the ring. When the prosthesis is subjected to the dynamic stresses, this spherical part is compressed first, thus it increases the one way function making impossible the expulsion of the male part.

Figure 21:
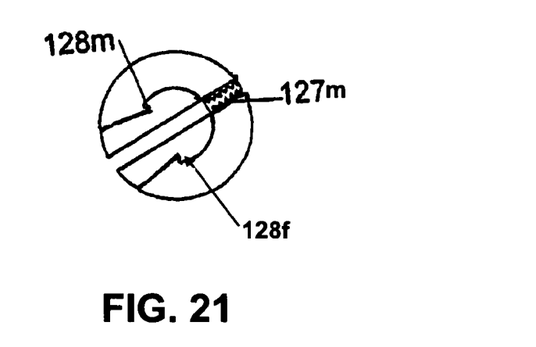
FIG. 21 of sheet 8/8 shows the same prosthesis once the guidance stems are removed.
Figure 22:
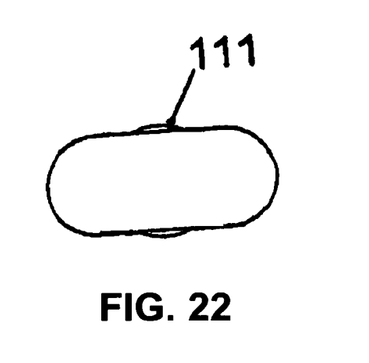
FIG. 22 of sheet 8/8 is a vertical cross-section of the prosthesis.
Figure 23:
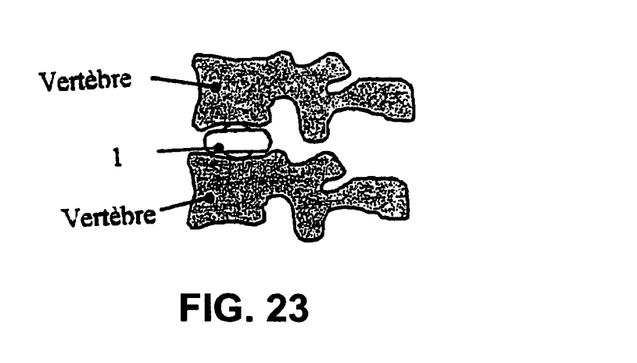
FIG. 23 of sheet 8/8 is a vertical cross-section of the installed prosthesis.

The female part can have a metal insert receiving the threaded rod 127m, which is visible under X rays. Once prosthesis 1 is in place, the position of the insert makes it possible to check the stability of the prosthesis over time, it also allows easy disassembly of the stem 21 once the prosthesis is installed.

All the embodiments which consist in introducing a nucleus prosthesis with its means of insertion in an osseous cavity, then to withdraw these insertion means, are a part of the invention and are claimed as such. They can comprise either the means described in the present invention, or equivalent means as soon as they make apparent possible cuts or removable means or provisional fixings.

The invention claimed is:

1. A nucleus prosthesis for insertion in an intervertebral cavity, the prosthesis characterized in that it comprises:
   a first and a second interlocking structural component, each made of a semi-rigid, deformable elastic material suitable for supporting a compressive load and in that, the second structural component inserts substantially within the confines of an envelope defined between surfaces of the first structural component;
   insertion tubes which guide the first structural component of the nucleus prosthesis into the to-be-filled intervertebral cavity and, after insertion, hold the first structural member in place; and
   a rigid stem connected to the first structural component via a connection, the rigid stem guiding the second structural component through the tubes, into engagement with a central cavity of the first structural component after insertion into the intervertebral cavity.

2. The nucleus prosthesis according to claim 1 characterized in that:
   the first structural component takes the form of a hollow sphere flattened at the poles and the central cavity is accessible via a deformable opening in the first structural component; and
   the second structural component is substantially a full sphere, which is able to pass through the deformable opening into engagement with the central cavity, in order to form an elastic block which cannot be expelled from its housing when the prosthesis is subjected to imposed mechanical forces.

3. The nucleus prosthesis according to claim 2 characterized in that a deformable opening of the first structural component cuts a sector through a thickness of the first structural component, the deformable opening having a constriction that prevents expulsion of the second structural component after introduction of the second structural component.

4. The nucleus prosthesis according to claim 3 characterized in that the second structural component comprises a fixation allowing the passage of a screw for fixing on the bone in order to better ensure good anchoring of the prosthesis.

5. The nucleus prosthesis according to claim 1 characterized in that the first structural member comprises a thread for receiving the rigid stem whose end has a corresponding thread, the aforementioned rigid stem also allowing the withdrawal of the rigid stem by simple unscrewing, once the prosthesis is in place.

6. The nucleus prosthesis according to claim 5 characterized in that the second structural component has the shape of a champagne cork serving as a one way device comprising a deformable fully spherical head and, optionally, a slightly extending cylindrical body.

7. The nucleus prosthesis according to claim 6 characterized in that anchoring of a male part in a female part is ensured by a one way shoulder which overlaps the male part and the female part.

8. The nucleus prosthesis according to claim 6 characterized in that a thickness of the second structural component slightly exceeds a thickness of the first structural component in order to, during dynamic stresses, initially compress the second structural component so as to better lock the second structural component into the central cavity.

9. The nucleus prosthesis according to claim 1 characterized in that an insert in the first structural component makes it possible, by X ray inspection, to check the stability of the prosthesis over time.

10. The nucleus prosthesis according to claim 9 wherein the insert is a cylindrical metal insert which is clearly distinguishable from the first and second structural components by X ray inspection, the insert having a visible orientation when viewed by X ray wherein the orientation of the insert indicates the orientation of the prosthesis.

* * * * *